US006575015B2

(12) United States Patent
Lechner-Fish et al.

(10) Patent No.: US 6,575,015 B2
(45) Date of Patent: Jun. 10, 2003

(54) SAMPLE AND CARRIER GAS PRE-HEAT SYSTEM FOR GAS CHROMATOGRAPH

(75) Inventors: Teresa Lechner-Fish, Katy, TX (US); Robert Jeffrey Runyan, Houston, TX (US)

(73) Assignee: Daniel Industries, Inc., Houston, TX (US)

( * ) Notice: Subject to any disclaimer, the term of this patent is extended or adjusted under 35 U.S.C. 154(b) by 0 days.

(21) Appl. No.: 09/841,412

(22) Filed: Apr. 24, 2001

(65) Prior Publication Data

US 2002/0166364 A1 Nov. 14, 2002

(51) Int. Cl.[7] .............................................. G01N 30/04
(52) U.S. Cl. ...................................................... 73/23.42
(58) Field of Search .......................... 73/23.42, 382 R; 95/8, 19, 82; 702/24

(56) References Cited

U.S. PATENT DOCUMENTS

| | | | | |
|---|---|---|---|---|
| 3,592,064 A | * | 7/1971 | Gether ..................... 73/382 R |
| 4,300,393 A | * | 11/1981 | Stearns ..................... 73/863.11 |
| 4,883,504 A | * | 11/1989 | Gerstel ............................ 95/8 |
| 5,163,979 A | * | 11/1992 | Patrick et al. .................. 95/19 |
| 5,668,735 A | * | 9/1997 | Dominguez et al. .......... 702/24 |
| 5,711,786 A | * | 1/1998 | Hinshaw ......................... 95/82 |

* cited by examiner

*Primary Examiner*—Helen Kwok
*Assistant Examiner*—Jay L Politzer
(74) *Attorney, Agent, or Firm*—Conley Rose P.C.

(57) ABSTRACT

A novel gas chromatograph includes suitably located back-pressure restrictors. In a preferred embodiment, each back-pressure restrictor consists of capillary tubing with a pressure drop across it controlled to be less than or slightly greater than 0.528. One embodiment places the backpressure restrictor upstream of an initial stream switching valve and downstream of sample pre-heat coil. Another embodiment places the backpressure restrictor downstream of the gas chromatograph's measurement element and its carrier pre-heat coil. In each case, only a controlled and predictable flow rate is achieved, both regulating the flow rate through the system and back pressuring fluid to remain in the respective pre-heat coils to achieve ideal temperature.

32 Claims, 13 Drawing Sheets

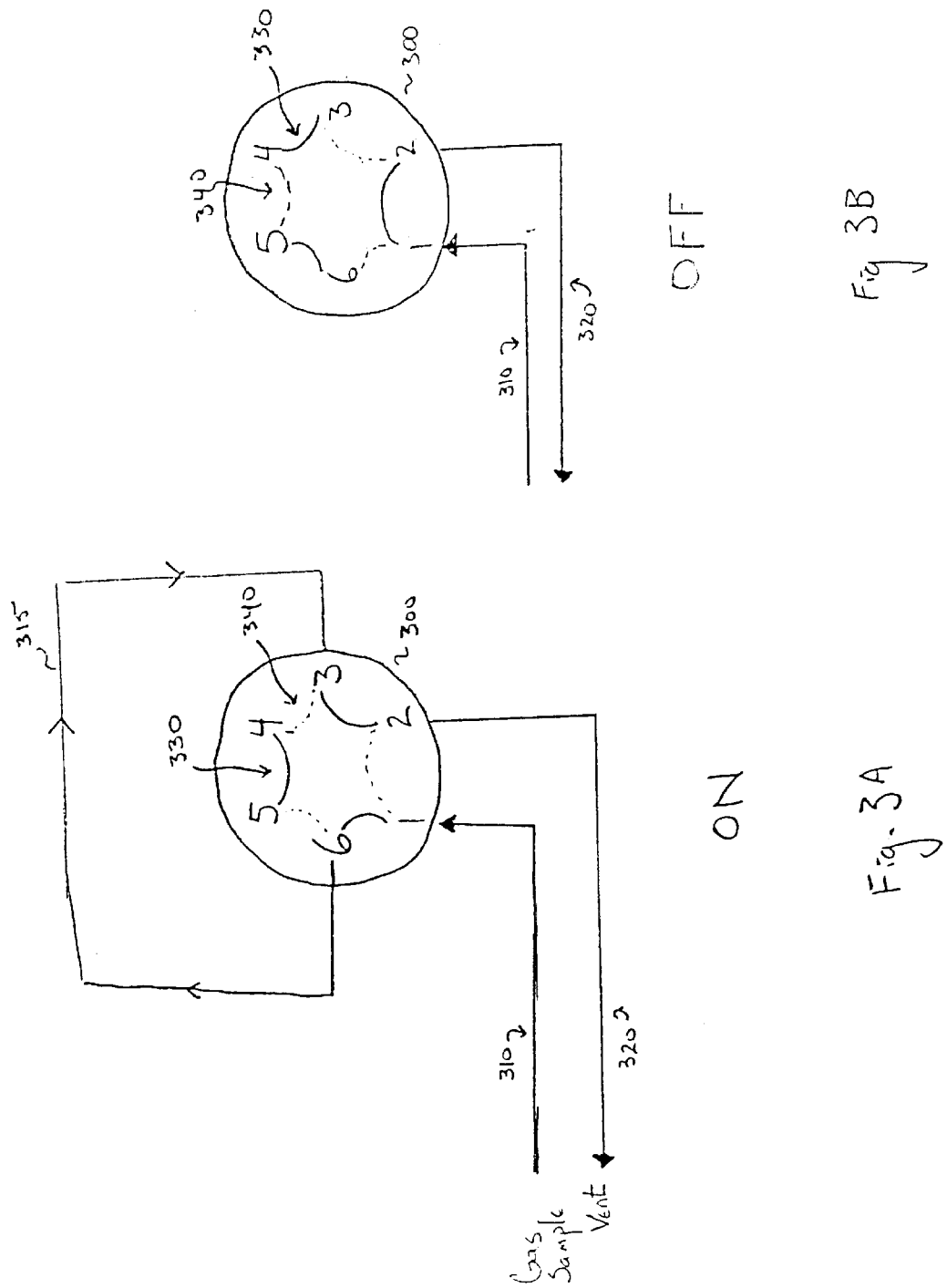

SAMPLE AND CARRIER GAS PRE-HEAT SYSTEM FOR GAS CHROMATOGRAPH

BACKGROUND OF THE INVENTION

The field of process chromatography is concerned with analyzing gas samples flowing through a process pipeline. A sample from a gas pipeline may be taken by use of a sample probe or other sampling device, which then provides the sample to a gas chromatograph. The gas chromatograph separates the sample into its individual components, using a variety of detectors to analyze the concentration of the resulting component bands in the sample. In the oil and gas industry the knowledge of what fluid is being transported by the pipeline is useful for a variety of purposes, such as source identification and custody transfer.

FIG. 1 shows a known gas chromatograph system (not to scale). Gas flows through a process pipeline 110, a sample of which is taken by a sample probe 120 prior to being introduced to gas chromatograph (GC) 100. The gas sample may be filtered and heat traced generally along tubing 130 before flowing into gas chromatograph 100. Heating may be required for gases that may condense into a part gas, part liquid flow at cooler temperatures. After being analyzed by the gas chromatograph, the gas sample is either returned into the process pipeline 110, or vented to the atmosphere. As used herein, the term gas chromatograph is being used in its broad sense, to include what is traditionally known both as the sample handling system and as the carrier pre-heat system.

Referring to FIG. 2, gas chromatograph 100 includes valve assembly 210 connected to multiple columns 220 and detectors 230, in this case, thermal conductivity detectors (TCD's). A gas sample generally follows path 240 through valve assembly 210, columns 220 and TCD's 230. The valve assembly allows the selection of columns 220 which contain a liquid phase, or porous polymer, or other material. Two types of columns are: 1) packed columns, filled with a liquid coated solid support or porous polymer; and 2) capillary columns, coated with a liquid or porous polymer. In either case, these materials act to separate the gas sample into multiple fractions, each fraction that is to be analyzed being sequentially directed to the TCDs 230. For example, a gas sample may contain various molecular weight hydrocarbon components such as ethane, methane, and heavier molecules. Ideally, each of these components would be analyzed individually. The resulting analysis could be normalized to minimize the effects of varying sample size from one injection to the next. In general, column 220 separates the gas sample so that more volatile components would elute from the column first, followed by less volatile components (although the use of valve switching may cause the components not to elute at the detector in that order).

Referring to FIGS. 3A and 3B, the operation of a sample valve is shown. Valve 300 includes a plurality of valve ports, labeled 1–6. Incoming line 310 provides a gas sample to valve 300. Exhaust line 320 expels the gas sample from the valve 300. Solid lines 330 show open passages between ports, whereas dotted lines 340 indicate blocked passages between the ports.

A solenoid (not shown) places valve 300 into either an ON position, as shown in FIG. 3A, or an OFF position, as shown in FIG. 3B. When a valve is in the ON position, sample gas flows from incoming line 310, through port 1 to port 6, through line 315 and finally through port 3 to port 2 and out exhaust line 320. When the valve is in the OFF position, sample gas flows from incoming line 310, through port 1 to port 2 and out through exhaust line 320. At the same time, carrier gas flows through port 5 to port 6 into line 315 where it displaces the sample gas. The carrier gas then flows from port 3 to port 4 and injects the sample onto the column. Of course, the designation of OFF versus ON is somewhat arbitrary and the opposite nomenclature could also be used.

FIG. 3C illustrates how a pair of valves may operate either alone or in combination with additional valves (not shown). A first valve 300 includes an array of six valve ports. A second valve 350 also includes an array of six valve ports. Associated tubing 310, 315, 320, 325 and 390, and columns 360 and 370 are also shown as well as dual TCD's 380.

Incoming line 310 is attached to a sample transport line (not shown). When first valve 300 is in an OFF position, gas sample flows from incoming line 310 to port 1 to port 2 of the valve 300 and out exhaust line 320. When valve 300 is in an ON position, however, gas sample flows from port 1 to port 6 and then through sample loop 315. That gas then flows from port 3 to port 2 of valve 300 and is expelled out exhaust line 320. At this time, the sample loop 315 is filled with a gas sample. This means that, if valve 300 is turned OFF at this time, a gas sample is trapped within the sample loop 315.

Turning now to valve 350, when it is in an OFF configuration, carrier gas flows from carrier gas input line 390 through port 2 of valve 350, to port 1 and then through carrier tubing 325. At this time, valve 300 is also in an OFF configuration, so that the carrier gas in tubing 325 is forced through port 5 to port 6 and through gas sample tubing 315. Consequently, this action forces the gas sample down column 360 via ports 3 and 4. The gas sample can then additionally be forced through column 370 and into the dual TCD 380 via ports 4 and 3. Thus, the valves may be connected in series to form "channels." Each channel feeds into a corresponding thermistor pair (a measurement thermistor and a reference thermistor), which measures the amount of a component in the process sample. Alternatively, downstream analyzer valves can be arranged in the system to select a desired column or detector. The graph on which the data are presented has a series of peaks corresponding to the detected components (such as ethane, methane, etc.), and is generally referred to as a chromatogram.

FIG. 7 shows an example of a chromatogram. As various molecules elute from the columns 460 based upon their volatility, they are measured by a concentration-dependent detector such as a thermal conductivity detector (TCD), a flame photometric detector (FPD), a photoionization detector (PID), a helium ionization detector (HID), or an electrolytic detector. The measured values appear on the chromatogram as a series of peaks. The peak maximum corresponds to the absolute retention time (i.e. time elapsed from injection of sample) for each component in the gas chromatograph system, with the area under each peak being related to the concentration of that component in the sample. To operate the system most efficiently, the valve switching directs the samples from column to column at predetermined times. The columns are sized to provide adequate time between critical components (i.e. for valve switches).

FIG. 4 illustrates a simplified gas chromatograph 400 as is broadly known in the art. Sample valve 410 connects to sample-in line 420, sample out line 430, carrier-in line 440 and column line 450. Sample-in line 420 connects to sample shut-off valve 470 upstream of the sample valve 410. Immediately upstream of sample shut off, sample in line 420 connects to a sample pre-heat coil. Further upstream, sample-in line 420 connects to, e.g., a process pipeline (not shown). Downstream of the sample valve 410, column line 450 connects to column 460. Column 460, in turn, connects downstream to the remainder of the gas chromatograph, including TCD 480, with measurement line 481 and reference line 482.

During operation, a sample of fluid is delivered from a process pipeline or similar source through sample-in line 420. Once the sample is inside the sample valve 410, sample shut off valve 470 is actuated, closing off sample valve 410 from the upstream sample source. At this time, the sample in the sample valve 410 is allowed to equilibrate with atmospheric pressure by exhausting or bleeding the excess sample through sample out line 430. At this time the sample valve 410 is actuated, changing the internal flow of the sample valve 410. Carrier-in line 440, holding pressurized carrier gas, such as helium, hydrogen, nitrogen or argon, is now in communication with the sample trapped in the sample valve 410. This carrier gas displaces the sample out column line 450 and to column 460.

One problem with the arrangement of FIG. 4, however, is the temperature variation of inlet sample gas. Variations in temperature between samples of fluid affect the amount of sample (i.e. number of moles) held in sample valve 410, and therefore carried to column 460. This affects the accuracy of the measurements downstream at the TCD's (or other detectors).

More specifically, from the Ideal Gas Law, it is known that:

$$PV=nRT \qquad (1)$$

Where,

P=pressure;

V=volume;

n=number of moles;

R=gas constant; and

T=temperature.

Due to a fixed-sized sample loop, the sample volume inside the sample valve 410 is essentially constant. Therefore, a first problem with known gas chromatographs is that the number of moles in the sample injection varies directly with sample pressure and inversely with sample temperature. Variations in temperature or pressure therefore change the number of moles in the sample, and this change in the number of moles impacts the reproducibility and analytical precision of the gas chromatograph. Consistent sample injections are especially important for chromatography applications that can't normalize the data, such as heartcut or backflushing of part of the sample to vent.

A second problem is "retention time drift" that arises from differences in temperature between the inlet sample and the carrier gas. FIG. 9 shows an example of retention time drift when the inlet sample temperature or carrier temperature is warmer than the column temperature. This is a problem because where the component peaks overlap or extend beyond the switching time for a corresponding analyzer valve, the offending portion of the curve is not measured by the chromatograph.

In process chromatography, it is important to have short analysis times to provide sufficient analytical feedback for process control. For this reason, the process chromatographer sets the switching times as close together as realistically possible to provide the fastest possible chromatograph, and so merely allowing more component separation (i.e. longer analysis times) is not a best-case solution.

It is desirable, therefore, to heat the inlet sample and carrier gas to the gas chromatograph temperature, usually chosen in the range of 80–85° C. with little variation. It has been difficult to heat the inlet gas to a consistent temperature, however. One effort involved placing a length of tubing inside a heated zone, while at the same time, coiling the tubing in a compressed corkscrew manner to conserve space. However, even heating of very long coils of tubing, such as 50-foot coils, does not reliably heat the inlet gas to the desired temperature. This is due to the fact that the ambient temperature of a process gas chromatograph varies from −18 to 55° C. Further, this approach is a less than ideal method of heating the inlet gas because the extra length of tubing results in additional costs, spatial requirements, and complexity when designing a heated zone for the gas chromatograph.

A related problem is variation in component retention time arising from fluctuations in the inlet carrier pressure. Since inlet pressure fluctuations affect the carrier flow rate, they also result in retention time drift. It is desirable therefore to eliminate or minimize these variations in inlet carrier pressure.

A third significant problem is that of "baseline drift." FIG. 8 shows the effects of baseline drift on a simplified chromatogram. The drift has been exaggerated to illustrate the measurement error. The curve produced by the measurement element, such as a TCD, is based upon the actual baseline. However, the actual baseline has "drifted" or dropped below the assumed baseline. Because the peak integration algorithms make certain assumptions regarding the area underneath the curves, including determining the assumed baseline, an error is introduced by baseline drift. In particular, the peak integration algorithms fail to detect any portion of the curve that falls above the actual baseline yet below the assumed baseline.

Baseline drift occurs where there is a temperature difference between measurement and reference thermistors, filaments or other detector elements. Referring again to FIG. 4, TCD 480 includes measurement line 481 and reference line 482. A thermal conductivity detector operates based on measuring the thermal conductivity of the fluid at the measurement point as compared to the fluid at the reference point. Thus, the inlet carrier gas temperature can affect the measurement stability of the thermal conductivity detector and any fluctuation in temperature of the reference relative to measurement results in detector baseline drift. However, although it is therefore important that the fluid flowing through the measurement and reference lines are at the same temperature, variations are common due to the fact that the ambient temperature of a process gas chromatograph varies from −18 to 55° C. As previously described, the preheat coils for the referenced inlet carrier gas are unable to achieve the desired temperature.

A fourth significant problem is that of "band spreading". Unlike retention time drift, where the entire curve shifts to one side or another, band spreading involves the widening of the entire band curve. FIG. 11 (not to scale) shows the effects of band spreading on a simplified chromatogram. Curve 1101 is a chromatogram curve without band spreading, while curve 1102 is the corresponding curve with band spreading.

As can be appreciated, a great amount of information can be determined from an accurate chromatogram curve. Referring still to FIG. 11, in the Figure the term t represents time, $t_r$ is retention time, h is height, $W_b$ indicates the width at the base of the curve, $W_{0.5}$ represents the width of the curve at the half-height, $W_i$ is the width of the curve at the inflection point, and 0.607 h shows the height of the curve at the inflection point. With band spreading, it is more difficult to identify these points accurately. Further, if the band curve becomes spread beyond the desired switching time, a portion of the curve would not be measured by the chromatograph. Alternately, the valve switching time could be delayed for the elution of the component but this would lead to longer analysis times. As mentioned previously, it is important to have short analysis times in process chromatography to provide good process control. Thus, excessive band spreading results in measurement errors or longer analysis times.

The problem of band spreading arises from gas decompression and carrier velocity acceleration as the sample travels through the column. As a result, most of the separation of components completes at the front of the column. Historically, chromatograph research has focused on developing small diameter capillary columns to compensate for this problem. However, this solution has been unsatisfactory because the complexity of the gas chromatograph varies directly with column diameter and the reliabilty varies inversely. Gas chromatographs with very small column diameter (i.e. <0.25 mm ID) are impractical for process (on-line) applications.

As can be seen, a number of problems exist with current gas chromatographs and a gas chromatograph is needed that solves these and other problems. The ideal process gas chromatograph would be both fast and accurate, eliminating or severely reducing many of the measurement errors known in the prior art. It would also be simple and inexpensive to manufacture. In a perfect world, the device or method that solves these problems would do so on its own, requiring little human supervision or maintenance. It would also have considerable longevity, including being sturdy and not prone to breakage.

SUMMARY OF THE INVENTION

A first embodiment of the invention is a sample handling system for a gas chromatograph, including a back pressure restrictor for the transport of a constant flow rate of fluid sample, a valve attached to the downstream end of the back pressure restrictor, and a separation column attached to the valve for eluting the sample into component parts. Preferably, the backpressure restrictor is capillary tubing. Ideally, the ratio of the fluid outlet pressure of the capillary tubing to the inlet pressure of the capillary tubing should be maintained at less than 0.528 to attain critical (i.e. laminar) flow. Although critical flow provides the maximum benefit, a pressure ratio approaching 0.528 from above would provide some benefit. Even more preferably, the sample handling system includes an insulated region having a heater, with the sample of pre-heat tubing being inside the insulated region and being upstream of the capillary tubing. The valve in the system may be an initial sample valve in the flow of the fluid sample through the system.

A second embodiment of the invention is a gas chromatograph including a measurement element with reference and component measurement locations, a transport line carrying carrier fluid and attached to the reference measurement location, carrier fluid pre-heat tubing connected to the transport line to warm the carrier fluid, and a back pressure restrictor connected to, and downstream of, the carrier fluid pre-heat tubing. Ideally, the backpressure restrictor is capillary tubing having an outlet to inlet pressure ratio of less than 0.528. Again, a pressure ratio approaching 0.528 from above would provide some benefit.

A third embodiment of the invention is a sample handling system including a separation column to separate a fluid sample into component parts, a measurement device downstream of the column, and a back pressure restrictor between the column and the measurement device. Preferably, the restrictor is capillary tubing.

BRIEF DESCRIPTION OF THE DRAWINGS

FIG. 3A is a schematic diagram of a valve in an OFF configuration;

FIG. 3B is a schematic diagram of a valve in an ON configuration;

DETAILED DESCRIPTION

Figure 1:
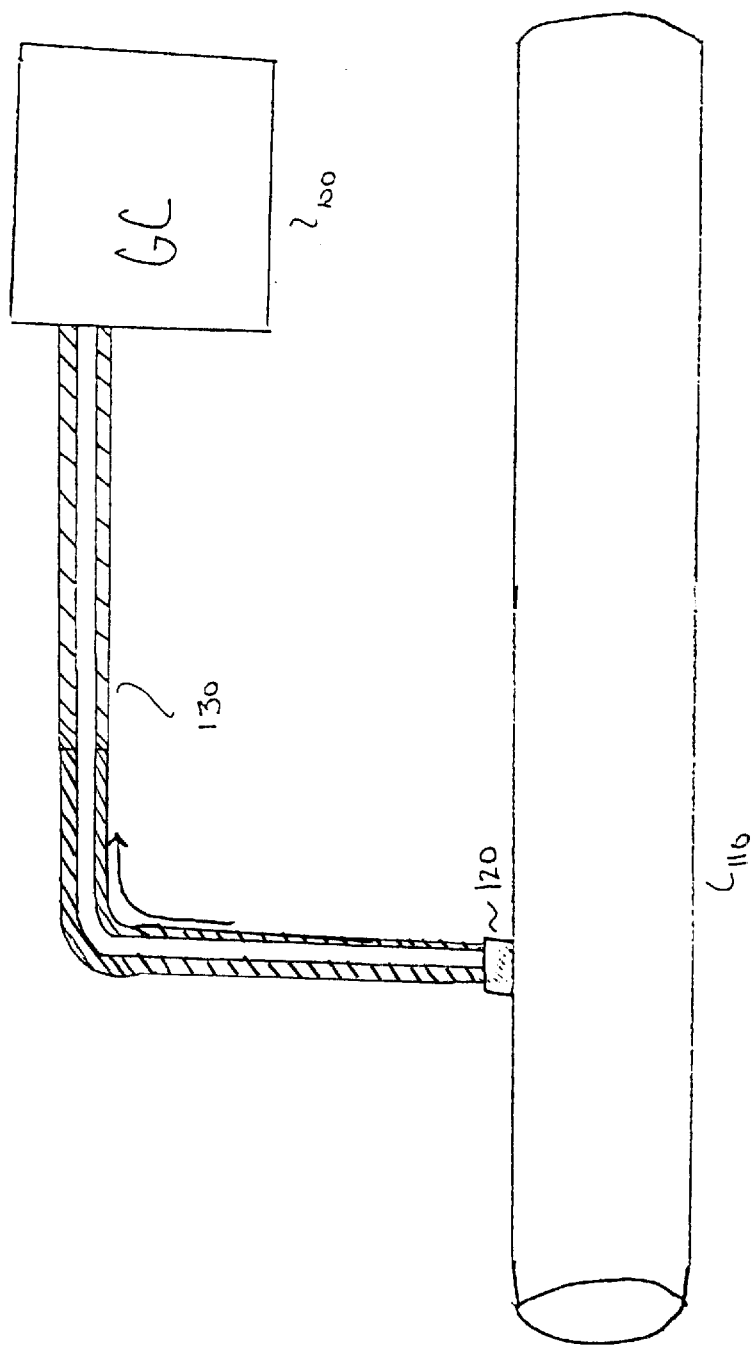
FIG. 1 is a simplified diagram of a gas chromatograph system.
Figure 2:
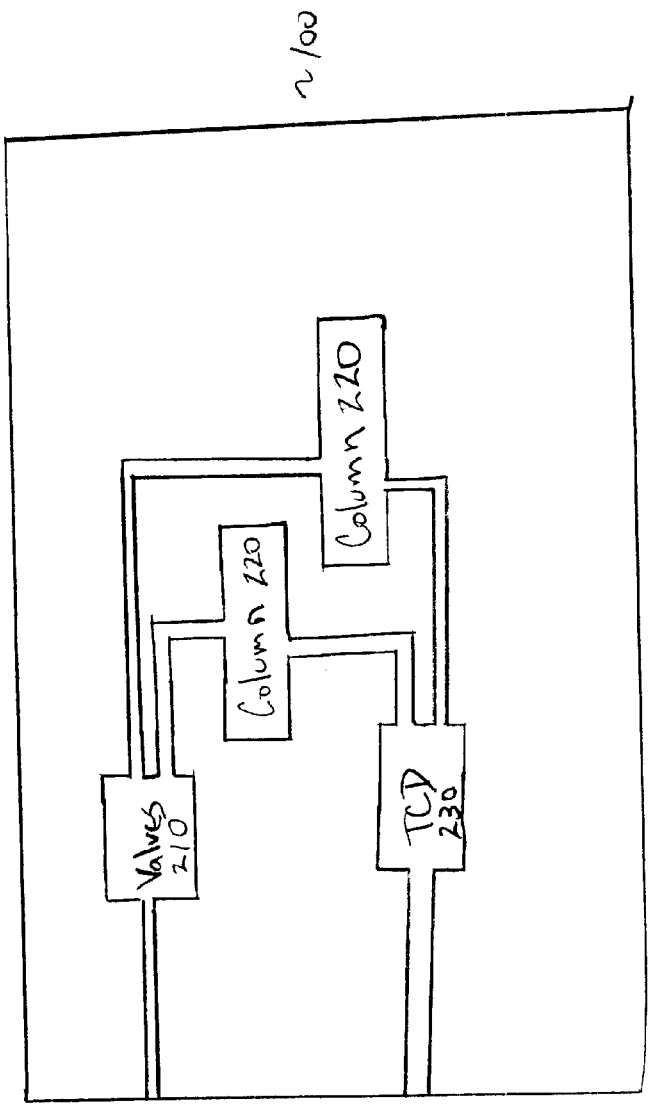
FIG. 2 is a simplified schematic of a gas chromatograph.
Figure 3C:
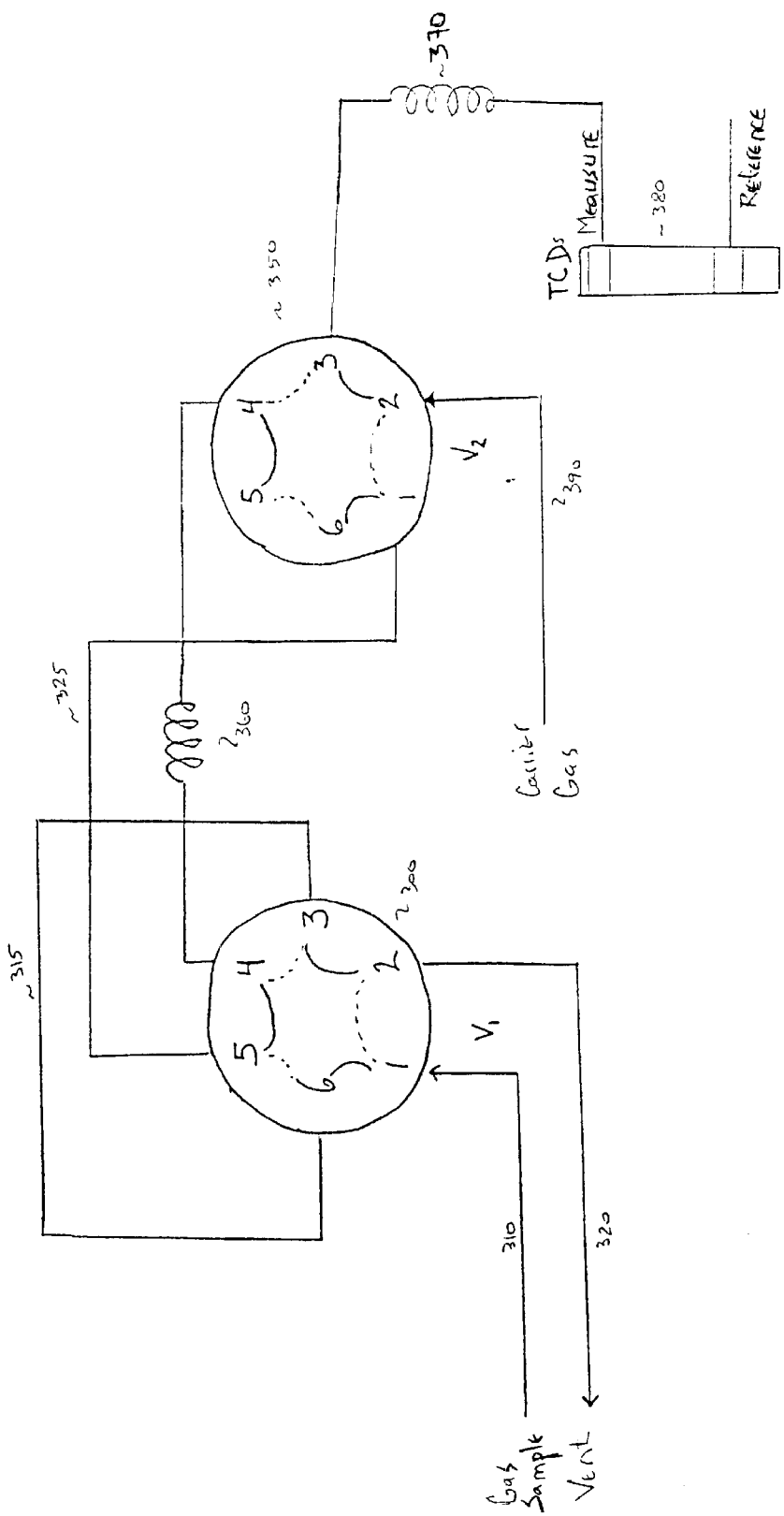
FIG. 3C is a schematic diagram of a multiple valve system for analyzing a sample.
Figure 4:
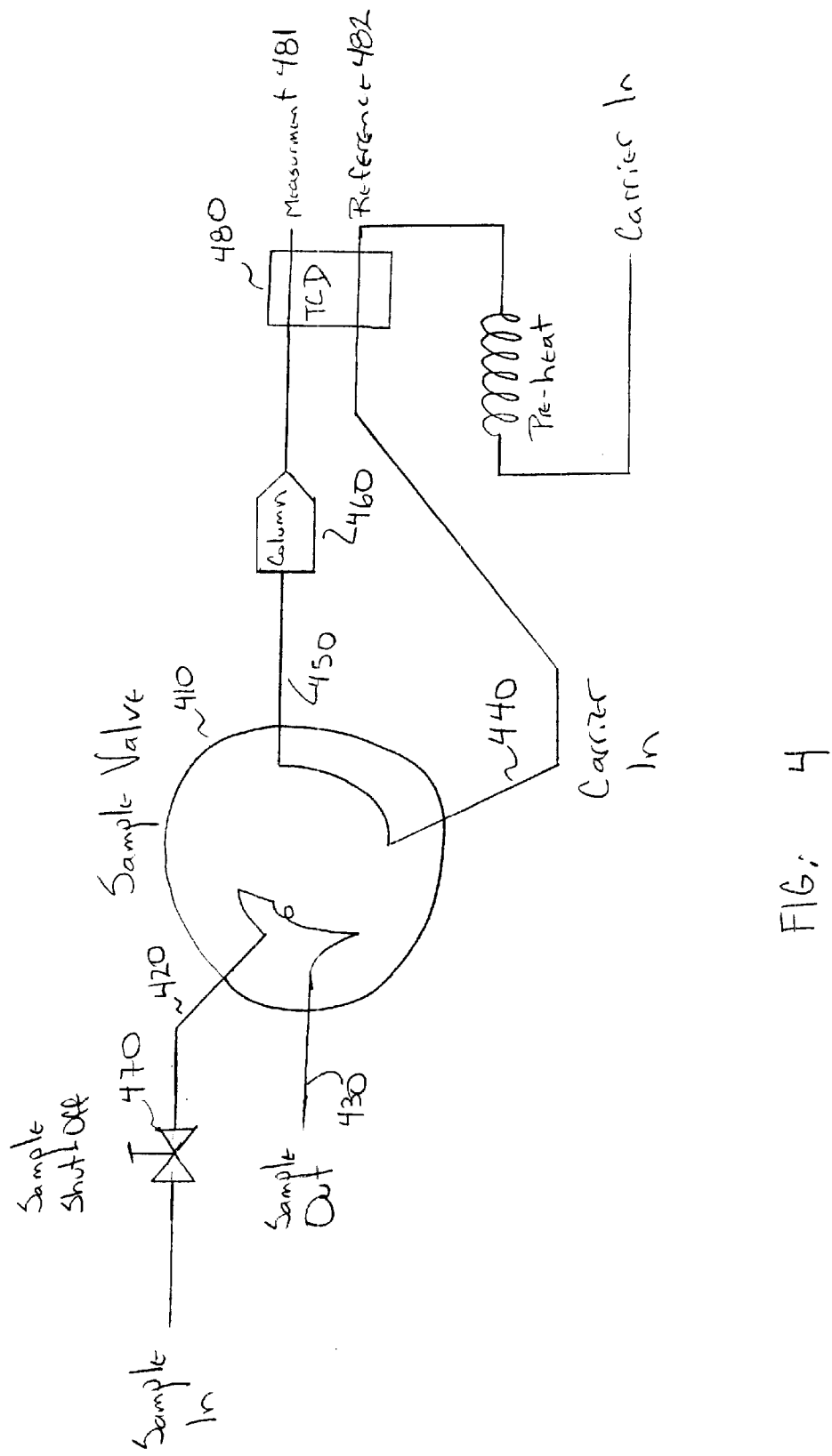
FIG. 4 is a schematic diagram of a simple gas chromatograph.

Embodiments of the invention ameliorate the problems discussed above. Examination of the mathematics underlying column and chromatograph efficiency illustrates principles used by the invention to achieve a more accurate chromatograph. From the Van Deemter Equation for packed columns, it is known that:

$$h=2\lambda d_p+2\gamma D_g fj/u+\omega d_p^2 fu/D_g j+2kd_f^2 u/[3(1+k)^2 D_1] \qquad (2)$$

In other words, equation (2) may be restated as:

h=eddy diffusion+longitudinal diffusion+resistance to mass transfer in the mobile phase+resistance to mass transfer in the stationary phase.

From the Golay-Gidding Equation for capillary columns, it is known that:

$$h=2D_g fj/u+(11k^2+6k+1)r_c^2 fu/[24(1+k)^2 D_g]j+2kd_r^2 u/[3(1+k)^2 D_1+\partial^2 u^2/(1+k)^2 L \qquad (3)$$

In other words, equation (3) may be restated as:

h=longitudinal diffusion+resistance to mass transfer in the mobile phase+resistance to mass transfer in the stationary phase+extra column effects.

Where, $h$=column efficiency defined as height equivalent to a theoretical plate $\lambda$=approximately 0.5, distribution factor $d_p$=particle diameter γ=approximately 0.7, obstructive factor due to the tortuous path taken by the solute molecule $D_g$=diffusion coefficient of the solute molecule in the gas phase $f=(9/8)[(P^4-1)(P^2-1)/(P^3-1)]$, Gidding plate height correction (gas expansion) factor, where $P=p_i/p_o$, where
 $p_i$=inlet pressure, and
 $p_o$=outlet pressure $j=(3/2)(P^2-1)/(P^3-1)$, James Martin compressibility factor, where $P=p_i/p_o$ u=mobile phase (carrier gas) linear velocity ω=approximately 0.002 to 5, packing factor to correct for radial diffusion k=capacity factor (partition ratio) of the solute $d_f$=film thickness of the stationary phase $D_1$=diffusion coefficient of the solute in the stationary phase σ=variance due to extra column effects L=length of column The maximum column efficiency is obtained when h is minimized. The largest contributing factor to h in equation (2), column efficiency, is the resistance to mass transfer in the stationary (liquid) phase of the packed columns (and for capillary columns with heavier film thickness (i.e. >0.25 microns)). Looking at equation (2), there is a variable in the resistance to mass transfer of the stationary phase term (i.e. $2kd_f^2u/[3(1+k)^2D_1]$) that may be controlled. In particular, the carrier gas linear rate, u, may be controlled. Therefore, for this type of column, column inefficiency typically varies directly with the mobile phase (carrier gas) linear velocity. Since inlet pressure is the driving force behind the carrier linear velocity, fluctuations in inlet pressure typically lead to variations of component retention times.

For capillary columns with light film thickness (i.e. <0.25 microns), the resistance to mass transfer in the mobile phase predominates. Looking at equation (3), there are three variables in the resistance to mass transfer in the mobile phase (ie. $(11k^2+6k+1)r_c^2fu/[24(1+k)^2D_g]$) that may be controlled. In particular, the column efficiency, h, is once again directly related to the carrier gas linear velocity, u. Again, since inlet pressure is the driving force behind the carrier linear velocity, fluctuations in inlet pressure typically lead to variations of component retention times.

In addition, in equation (2) and (3) both the gas expansion factor, f, and the compressibility factor, j, are dependent upon P, the ratio of the inlet pressure to the outlet pressure. Using L'Hopitals Rule, the limit of the gas expansion factor as the pressure ratio approaches unity can be calculated as, $$\lim f(P \to 1)=1$$

Similarly, the limit of the compressibility factor can be calculated as, $$\lim j(P \to 1)=1$$

As can be seen, from Equation (2) for packed columns, minimizing the pressure ratio will result in minimizing the longitudinal diffusion and resistance to mass transfer in the mobile phase terms. As the pressure ratio approaches unity, $$\lim h(P \to 1)=2\lambda d_p+2\gamma D_g/u+\omega d_p^2 u/D_g+2kd_f^2u/[3(1+k)^2D_1] \quad (4)$$

In other words, as the column inlet pressure approaches the column outlet pressure, an improvement is made in column efficiency because of improvements in longitudinal diffusion and resistance to mass transfer in the mobile phase. However, because resistance to mass transfer in the stationary phase usually predominates in packed columns, the improvement in column efficiency for packed columns by achieving a pressure ratio approaching unity is minimal.

For capillary columns with light film thickness, minimizing the pressure ratio will result in minimizing the longitudinal diffusion and resistance to mass transfer in the mobile phase terms. From Equation (3) for capillary columns, as the pressure ratio approaches unity, $$\lim h(p \to 1)=2D_g/u+(11k^2+6k+1)r_c^2u/[24(1+k)^2D_g]+2kd_f^2u/[3(1+k)^2D_1]+\sigma^2u^2/(1+k)^2L \quad (5)$$

Because the resistance to mass transfer in the mobile phase predominates for capillary columns with light film thickness (i.e. <0.25 microns), achieving a pressure ratio approaching unity would significantly improve column efficiency.

As noted above, it is also known that differences between the inlet sample temperature and the carrier gas temperature create measurement errors. Stated more technically, the resistance to mass transfer in the stationary phase is due to the kinetic rate of transfer of sample molecules between the mobile (carrier gas) and stationary (liquid) phases. The equilibrium between the two phases is established so slowly that the column always operates under nonequilibrium conditions. Since the diffusion coefficient varies inversely with temperature (i.e. the column efficiency varies directly with temperature), the component retention time drifts earlier when the temperature is too high. Likewise, the retention time drifts later when the temperature is too low.

Thus, although equations (2) and (3) assume a constant temperature and a constant gas inlet pressure, it may be inferred that column efficiency varies with temperature, carrier gas flow rate, and inlet pressure. Further, once the cause of the measurement errors is understood, as well how their magnitude is affected by changing variables in the gas chromatograph, it is necessary to formulate a method or structure to maintain a constant temperature and carrier gas flow.

Figure 5:
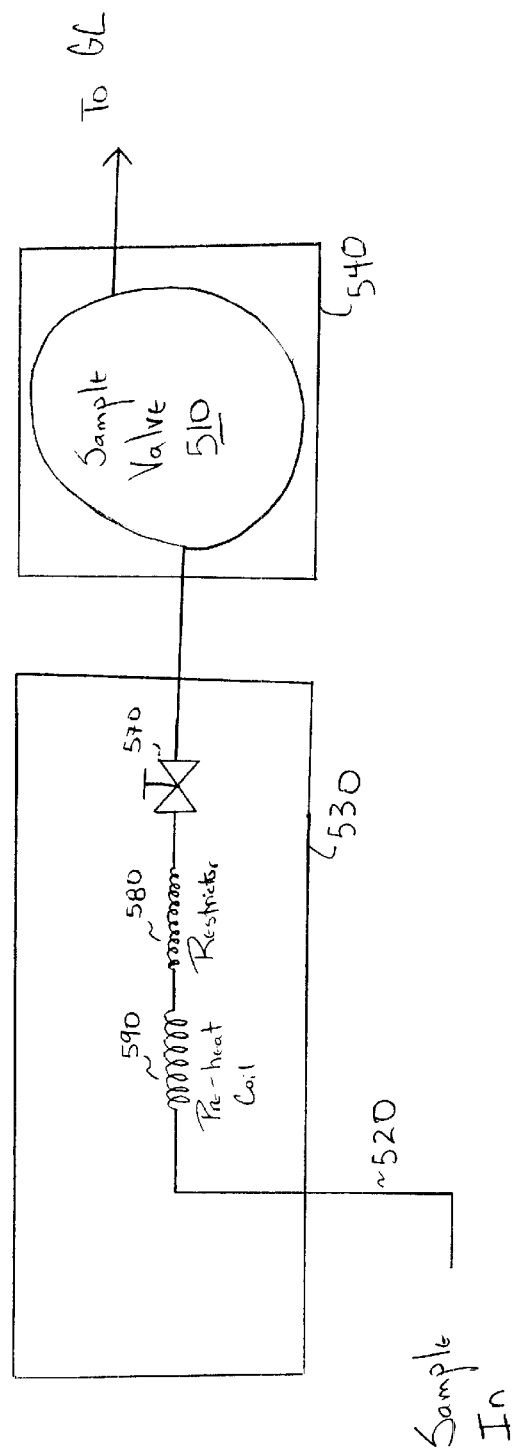
FIG. 5 is a schematic of a first embodiment of the invention.

It has been found that although pressure gradient is the driving force behind carrier linear velocity, improved efficiency can be achieved through proper placement and optimization of backpressure restrictors. FIG. 5 shows a first embodiment of the invention. A sample pre-heat system 500 includes a sample valve 510 connected to a sample-in line 520. Upstream of sample valve 510 along sample-in line 520 is sample shut off valve 570, backpressure restrictor 580, and pre-heat coil 590. Further upstream in the sample-in line 520 is the process pipeline, filtering and other possible conditioning (not shown). The sample valve 510, sample preheat coil 590, back pressure restrictor 580 and sample shut off 570 are in one or more ovens or insulated temperature maintenance zones 530, 540. The pressure of the sample gas from the process pipeline is normally reduced to a range of 15 psig–25 psig (pounds per square inch gauge) before delivering it to the gas chromatograph.

One important aspect of the pictured embodiment is the use of a backpressure restrictor 580 upstream of the columns, and preferably upstream of a sample valve 510. Where the gas chromatograph includes more than one sample valve connected serially, it is preferred to place the backpressure restrictor 580 upstream of all the sample valves, although this is not thought to be necessary to receive some benefit. The preferred backpressure restrictor is what is commonly termed capillary tubing (although capillary tubing is presently used for other purposes, such as a flame restrictor downstream of the column). To make the capillary tubing an effective backpressure restrictor, the ratio of the outlet pressure to the inlet pressure should be less than about 0.528. In other words, $$\frac{P_o}{P_i} \leq 0.528 \tag{6}$$

Where, $P_i$=inlet pressure; and $P_o$=outlet pressure.

Figure 6:
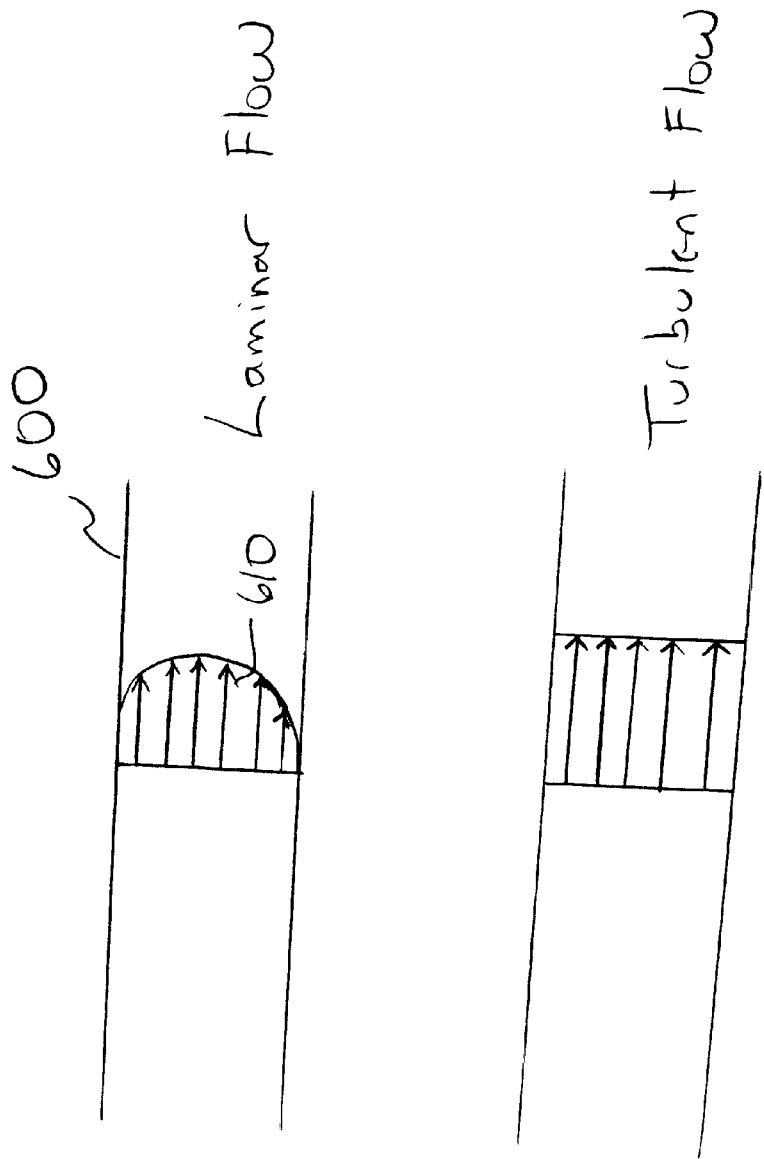
FIG. 6 is a diagram illustrating laminar versus turbulent flow.
Figure 7:
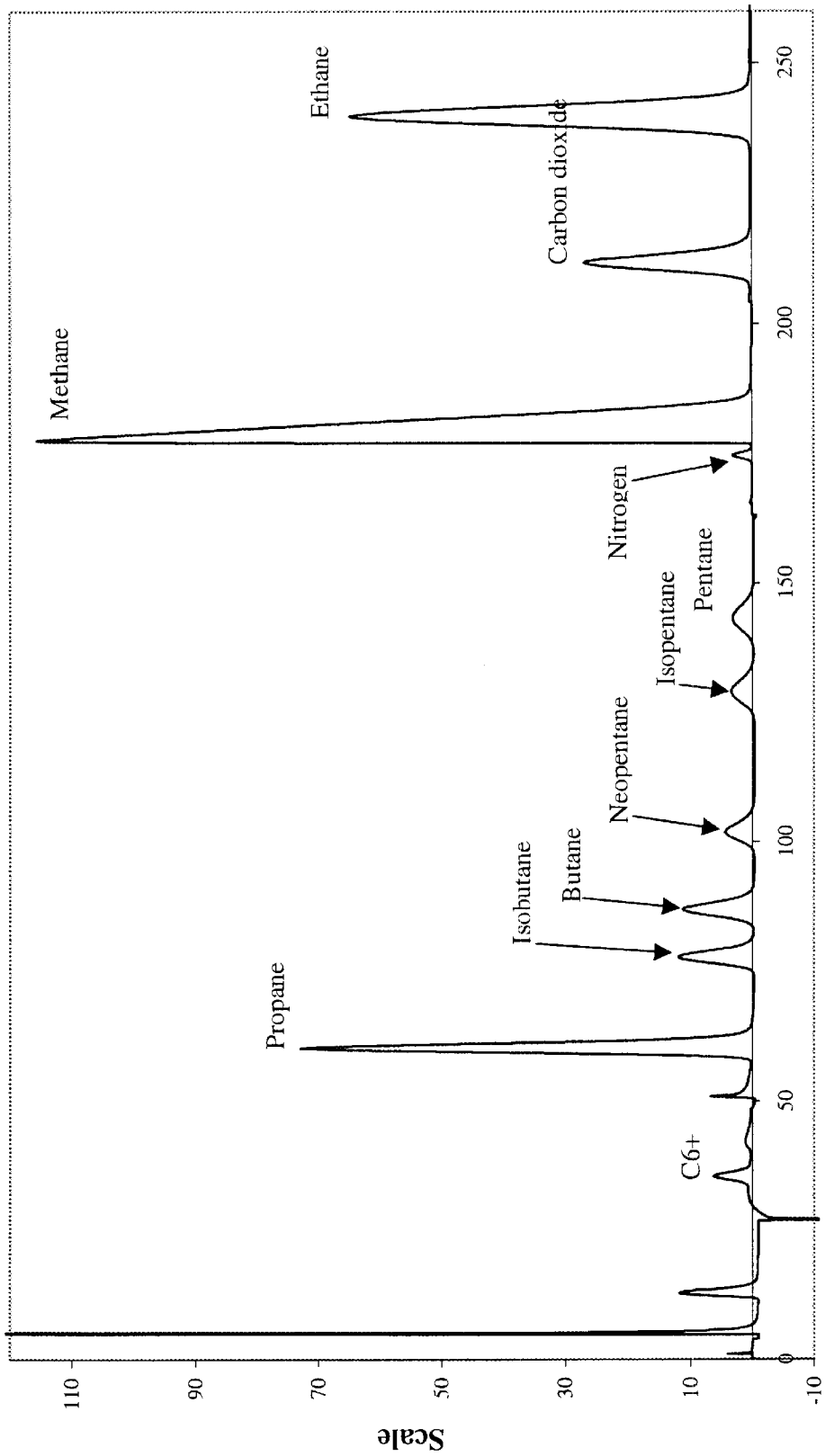
FIG. 7 is a chromatogram from a gas chromatograph.
Figure 8:
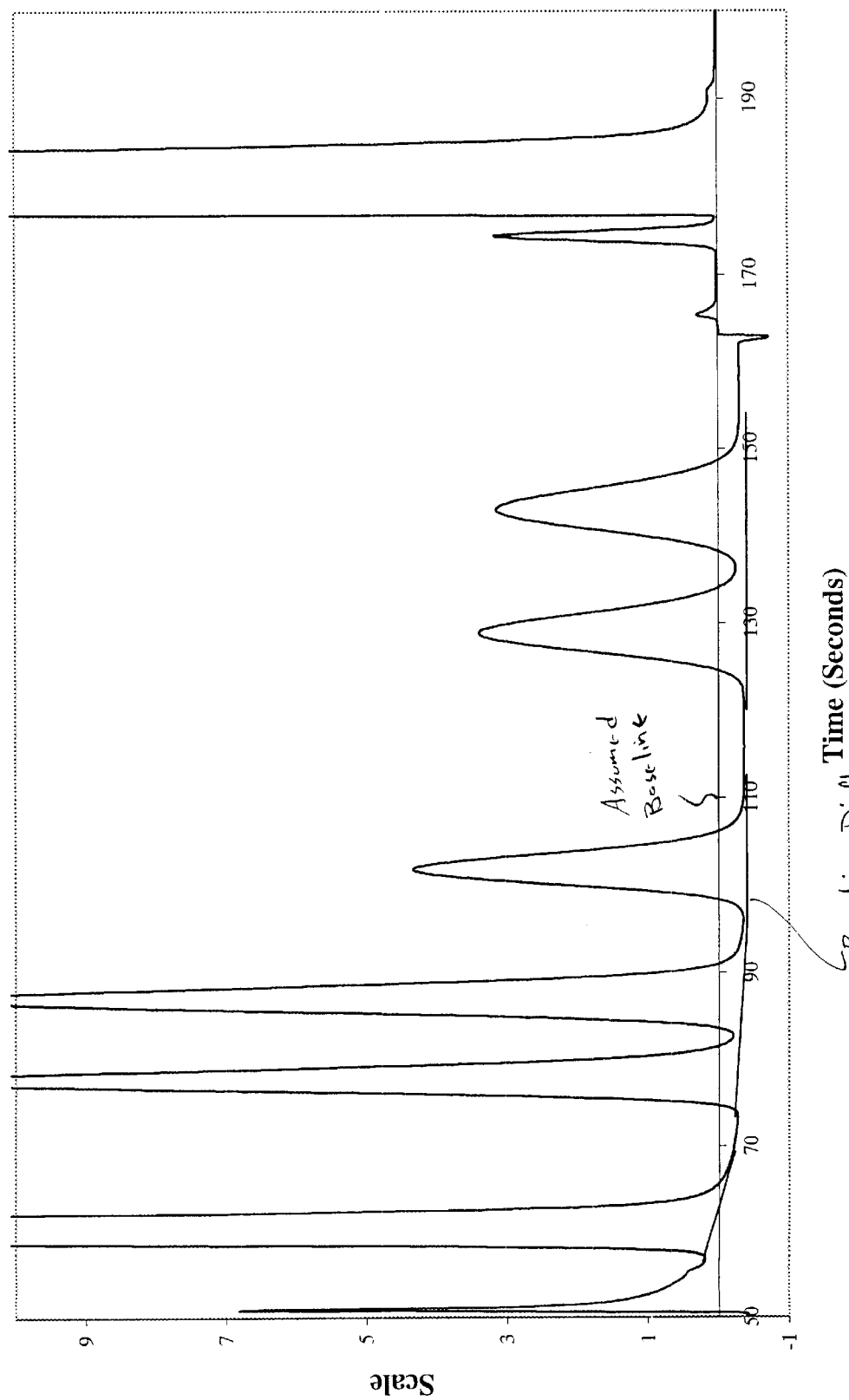
FIG. 8 is a simplified chromatogram showing baseline drift error.
Figure 9:
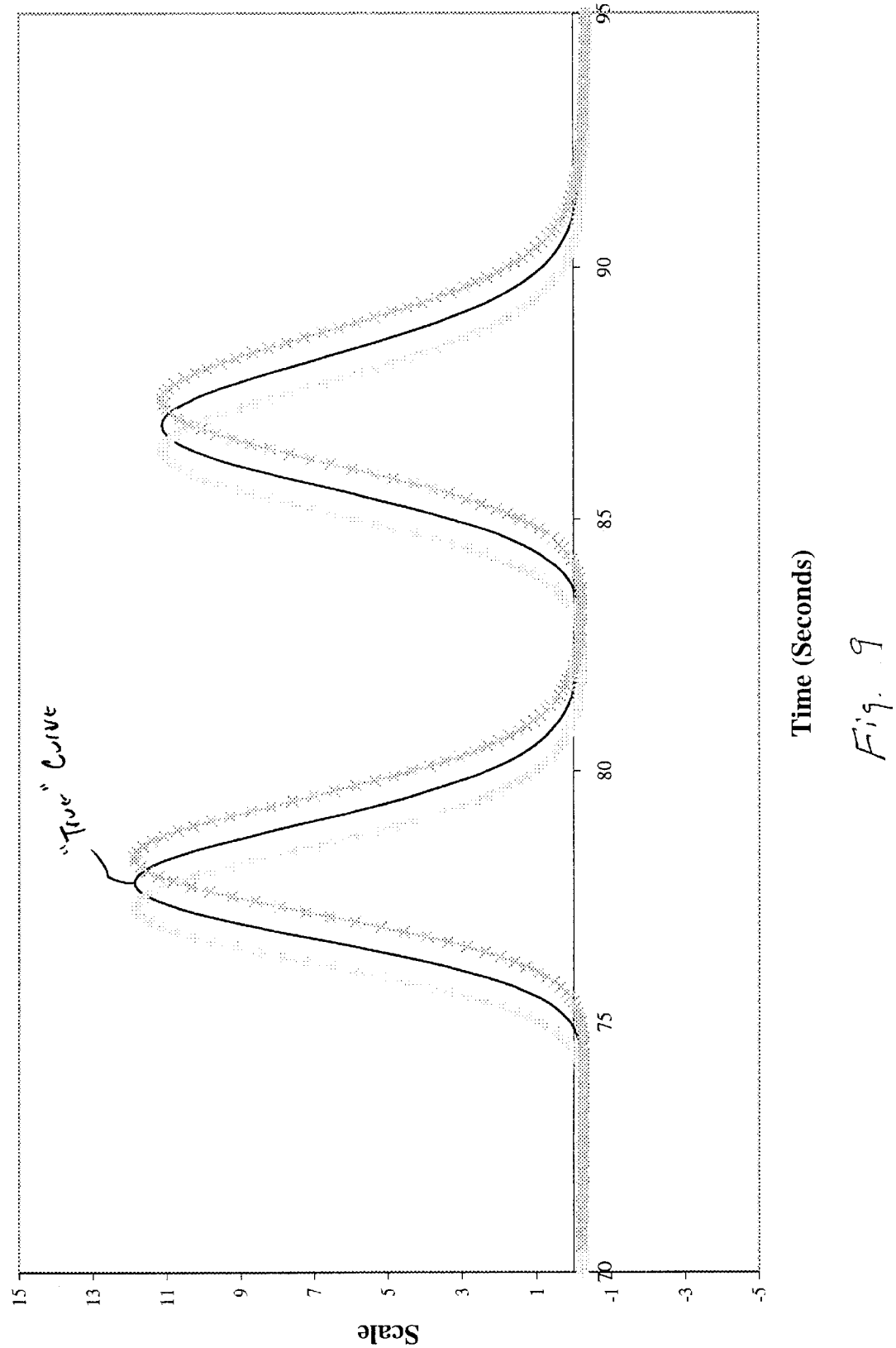
FIG. 9 is a simplified chromatogram showing retention time drift.

The interpretation of the term "about" is dictated by the purpose of the 0.528 pressure ratio. When the upstream to downstream pressure ratio is less than 0.528, critical (laminar) flow is achieved for the gas flowing through the capillary tubing. Laminar flow is a stable flow profile having a greater flow velocity at its center than at the tubing walls. FIG. 6 shows a not-to-scale example of laminar flow as contrasted to plug (turbulent) flow. Tubing 600 surrounds a set of velocity vectors 610 that are greater toward the middle of the tubing 600. More important to the invention is a second aspect of critical flow, a constant mass flow. In other words, despite changes in temperatures of 5–10° C. and changes in pressure of five psig (pounds per square inch gauge), the mass flow rate of gas to the column or columns downstream does not vary with any great significance. Even for temperature and pressure fluctuations beyond this range, the mass flow rate varies much less than it would otherwise. Thus, the use of capillary tubing regulates the mass flow provided to the detectors (such as TCD's) in the gas chromatograph and thereby increases the accuracy and reproducibility of the measurements in the gas chromatograph.

Capillary tubing is defined by its small inner diameter, which at maximum is 0.04" inner diameter. The pressure drop through the capillary tubing may be controlled either by adjusting the length or the inner diameter of the tubing. A longer length of tubing results in a greater pressure loss, as does a smaller inner diameter. Capillary tubing may have a 0.0625" outer diameter with a 0.004" to 0.04" inner diameter. Thus, for a given desired pressure drop, a shorter length of tubing is necessary. However, it should be noted that if the sample is not clean, particulates may be carried through the system and such particulates are more likely to plug small tubing than larger tubing. One envisioned embodiment of the invention would include 100 centimeters of 0.01-inch inner diameter tubing. Another has 20 centimeters of 0.05-inch inner diameter tubing. Larger tubing may also be selected, even beyond the range of what is generally considered capillary tubing. However, the resulting length of tubing larger than capillary tubing would generally be undesirably long, and the tubing inner diameter should not be so large as to destroy the tubing's function as a backpressure restrictor.

Another beneficial aspect to placing the pre-heat coil upstream of the backpressure restrictor is to maximize the time the fluid sample resides in the pre-heat coil. In other words, because the capillary tubing limits the maximum mass flow rate through the tubing, the gas flow upstream of the capillary tubing does not flow freely. What results is a longer residence time for the sample in the pre-heat coil. This extra time allows the sample to be heated more reliably and consistently to the desired 80–85° C. temperature, improving the reproducibility and accuracy of the gas chromatograph in another way.

Figure 10:
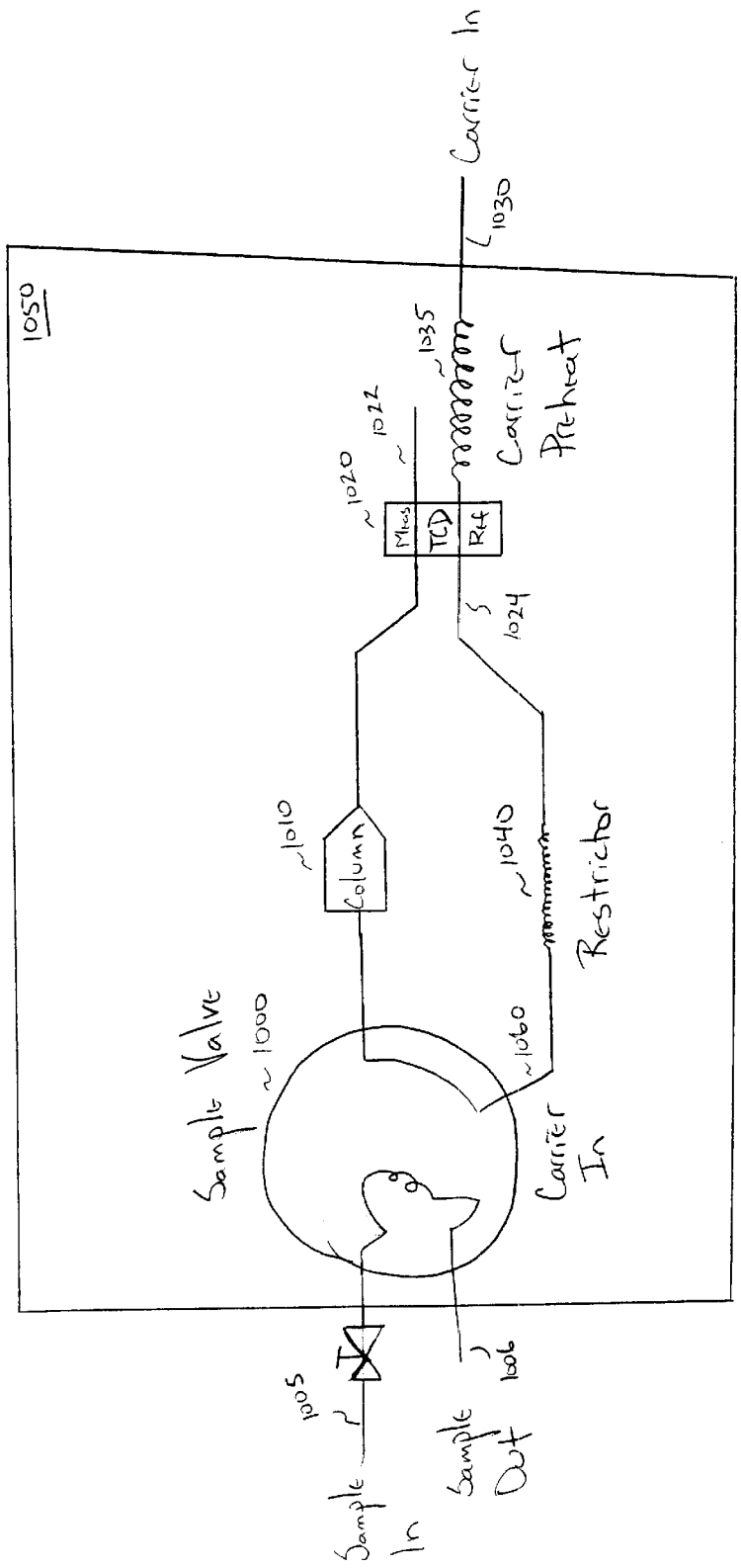
FIG. 10 is a schematic of a second embodiment of the invention.
Figure 11:
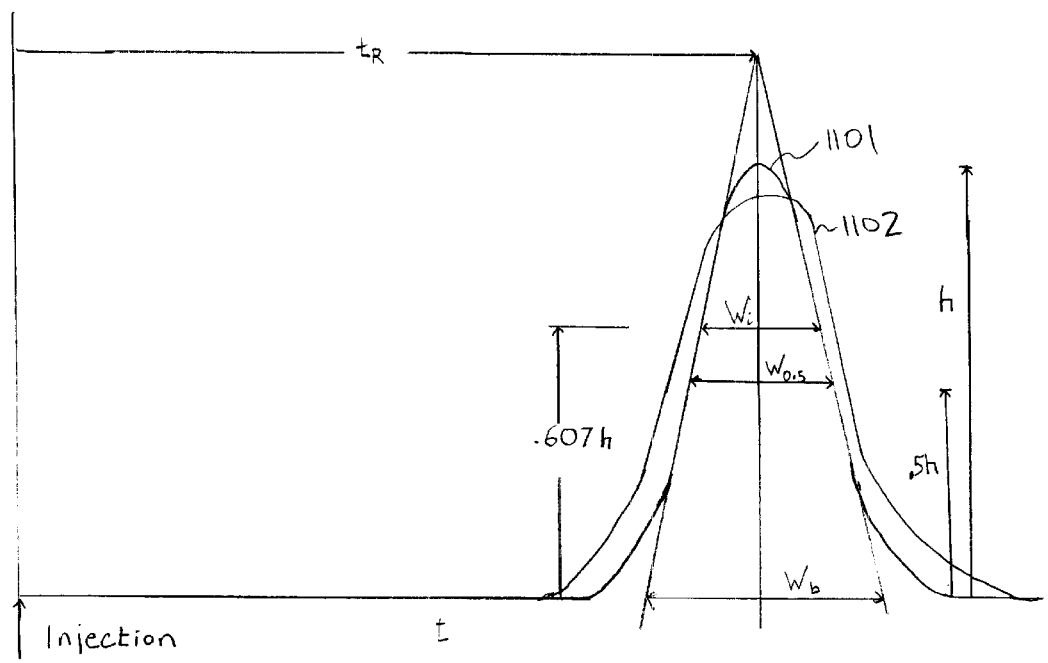
FIG. 11 is a simplified chromatogram showing band spreading.

FIG. 10 illustrates a second embodiment of the invention. A sample valve 1000 attaches to sample-in line 1005 and sample exhaust line 1006. Sample valve 1000 also attaches to carrier-in line 1060 on an upstream side, and column 1010 on a downstream side. Column 1010 attaches to the measurement line 1022 of TCD 1020. First carrier-in line 1030 is coiled along its length, resulting in a carrier pre-heat location 1035 in temperature oven 1050. Downstream of carrier pre-heat 1035 is the reference line 1024 of TCD 1020, and restrictor 1040. Restrictor 1040 connects to sample valve 1000 via carrier-in line 1060. As in the first embodiment, restrictor 1040 is preferably capillary tubing with a pressure drop ratio either lower than or slightly higher than 0.528.

This embodiment places the restrictor 1040 downstream of carrier pre-heat 1035, and preferably downstream of TCD (or other measurement element) 1020. By placement of the restrictor 1040 at such a location, only a limited, controlled, and constant amount of carrier gas passes through to the sample valve 1000 at any one time. In addition, restrictor 1040 creates an impediment to the free flow of carrier gas through the gas chromatograph, forcing the carrier gas upstream of the restrictor 1040 to remain inside oven 1050 and carrier pre-heat 1035 for a longer period. This longer period ensures proper heating of the carrier stream as it is being measured as the reference for the TCD 1020. By eliminating any temperature differential between the reference 1024 and measurement 1022 lines, baseline drift is expected to be greatly reduced.

Figure 12:
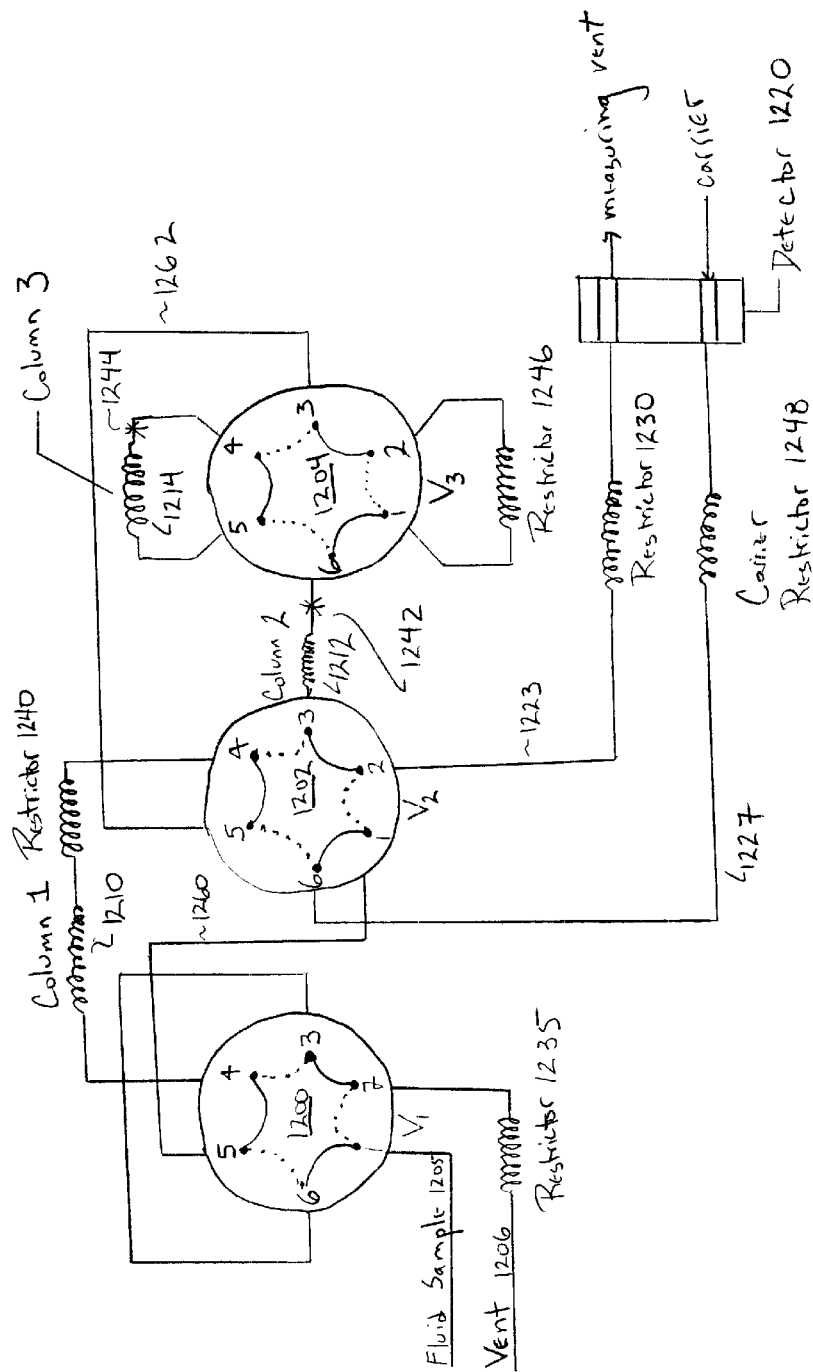
FIG. 12 is a schematic of a third embodiment of the invention.

FIG. 12 illustrates a third embodiment of the invention. A sample valve 1200 attaches to sample-in line 1205 and sample exhaust line 1206. Restrictor 1235 resides at some juncture in exhaust line 1206. Sample valve 1200 also attaches to carrier-in line 1260 on an upstream side, and to column 1210 on a downstream side. Column 1210 attaches to restrictor 1240, which in turn connects to port 4 of second sample valve 1202. Carrier-in line 1260 also attaches to sample valve 1202, but at port 1. Port 2 of sample valve 1202 connects to the measurement line 223 of detector 1220 via restrictor 1230. The reference line 1227 of detector 1220 connects to port 6 of sample valve 1202. Carrier restrictor 1248 resides on line 1227 between detector 1220 and port 6 of sample valve 1202.

This embodiment shows placement of backpressure restrictors at other advantageous positions in the chromatograph. A desirable location for a backpressure restrictor is a limited distance downstream of each column. By placement of a backpressure restrictor at the column output, an increase of pressure at the column output is achieved. This results in a column pressure ratio $p_i/p_o$ more closely approaching unity. The maximum effective distance for placing a backpressure restrictor can be estimated using the following expression:

Distance downstream (cm)=drift time (seconds)*carrier velocity (cm/second)

In a process GC, the peaks of the heavier components in a chromatogram may shift approximately 5–6 seconds across the range of ambient temperature. A reasonable goal is to reduce this peak shifting by an order of magnitude (i.e. 0.5–0.6 seconds), through minimizing longitudinal diffusion and resistance to mass transfer in the mobile phase as discussed previously. At the optimum practical carrier velocity of approximately 35–40 cm/s, (1.5–2 times the theoretical optimum carrier velocity), the maximum distance to achieve this goal is calculated to be about nine inches. A maximum of ten inches is realistic. These distances are generic for any diameter tubing so long as the optimum practical carrier velocity is used.

Another particularly desirable location for a backpressure restrictor is upstream of the detector, downstream of any valve switch, and downstream of the columns. Like placement of a backpressure restrictor just downstream of a column, placement of a backpressure restrictor just upstream of the detector backpressures the upstream columns. In addition, placement of a backpressure restrictor immediately upstream of the detector dampens pressure pulses that result at the detector from valve switches upstream of the detector. This reduction in pressure pulses helps to improve the accuracy of the detectors and the efficiency of the columns as shown mathematically above.

In process chromatography, it is important to have short analysis times to provide adequate process control. By improving the column efficiency, shorter columns can complete the desired separation resulting in faster analysis times. This technique has the added benefit of being simple and inexpensive to manufacture. The capillary restrictors are sturdy and not prone to breakage. In addition, because capillary tubing is readily available and is inexpensive, rapid acceptance by the industry is expected.

Referring again to FIG. 12, backpressure restrictor 1235 is located in the vent path of the initial valve switch 1200. Placement of a backpressure restrictor on the vent of the initial valve switch helps to regulate the sample size. For example, during calibration of a gas chromatograph at near sea level (such as in Houston, Tex.) the sample loop achieves atmospheric pressure at that location. Similarly, during calibration of a gas chromatograph at a mile-high elevation (such as in Denver, Colo.), the sample loop achieves a significantly lower atmospheric pressure resulting in fewer moles of sample being injected. Since the atmospheric pressure at these two elevations is not nearly the same and thus a calibration made in Houston would not be valid for Denver. In addition, atmospheric pressure also varies with weather conditions. This requires frequent calibration of each gas chromatograph, or normalization of the data. Unfortunately, the data cannot be normalized unless the entire sample is characterized.

Placement of a backpressure restrictor in the vent line backpressures the sample loop. This should reduce the variance in sample size and should also allow a reduction in the sample loop for a more compact injection. A gas chromatograph with calibrations more tolerant to changes in atmospheric pressure results. The suitability of any particular calibration for a given stream composition for differing atmospheric pressure is expected to be greatly enhanced (gas compressibility varies with composition). Even greater flexibility is expected to be achieved if multiple calibrations for different compositions could be stored in the gas chromatograph.

Many variations of the above teachings are within the scope of the invention. For example, any of the embodiments of the invention may advantageously be combined with any other. FIG. 13 is a schematic of a sample handling system including a back pressure restrictor upstream of a sample valve, a back pressure restrictor between a separation column and a measurement point on a measurement device, and a back pressure restrictor downstream of the reference point on a measurement device although only one switching valve was shown in the Figures, the teachings herein could be applied to gas chromatographs having many sample valves, and many different types of valves. In addition, the teachings of the invention are not limited to gas chromatographs. For example, the use of a backpressure restrictor may also be useful in moisture analyzers, etc. In addition, other backpressure restrictors may be utilized, such as sintered metal discs, inert packed tubing or needle valves.

What is claimed is:

1. A sample handling system for a gas chromatograph having at least one separation column, comprising:
   a back pressure restrictor with an upstream end and a downstream end, said back pressure restrictor carrying a fluid flow from said upstream end to said downstream end; and
   each of said at least one separation columns being attached to said downstream end of said back pressure restrictor to elute said fluid into component parts,
   wherein said fluid flow has a flow profile downstream of said backpressure restrictor and said backpressure restrictor controls said downstream flow profile to result in the transport of a near-constant mass flow of said fluid.

2. The gas chromatograph of claim 1, wherein said back pressure restrictor is tubing, the ratio of the pressure at said downstream end to the pressure at said upstream end being less than or slightly higher than 0.528.

3. A sample handling system for a gas chromatograph, comprising:
   a back pressure restrictor with an upstream end and a downstream end, said back pressure restrictor carrying a fluid flow from said upstream end to said downstream end; and
   a separation column attached to said downstream end of said back pressure restrictor to elute said fluid into component parts,
   at least one sample valve having an upstream end and a downstream end, said upstream end of said sample valve being attached to said downstream end of said back pressure restrictor and said downstream end of said sample valve being attached to an upstream end of said separation column;
   wherein said fluid flow has a flow profile downstream of said backpressure restrictor and said backpressure restrictor controls said downstream flow profile to result in the transport of a near-constant mass flow of said fluid.

4. The gas chromatograph of claim 2, further comprising:
   a pre-heat coil upstream of said tubing;
   an insulated oven encapsulating said pre-heat coil;
   a heater within said insulated oven.

5. The gas chromatograph of claim 3, wherein said at least one sample valve is an initial sample valve in encountered by the flow of said fluid in said gas chromatograph.

6. The gas chromatograph of claim 1, wherein said backpressure restrictor is in a sample handling portion of said gas chromatograph.

7. The gas chromatograph of claim 1, wherein said backpressure restrictor is in a carrier-pre-heat portion of said gas chromatograph.

8. The gas chromatograph of claim 1, wherein said backpressure restrictor is capillary tubing having an inner diameter of less than 0.04".

9. A gas chromatograph, comprising:
   a component measurement element including a reference measurement location and a sample component measurement location;
   a transport line attached upstream of said reference measurement location, said transport line to transport a flow of carrier fluid to said reference measurement location;
   a carrier pre-heat device connected to said transport line and upstream of said reference measurement location, said carrier pre-heat device transporting said flow of carrier fluid;

a back pressure restrictor connected to, and downstream of, said carrier pre-heat device, said back pressure restrictor being used to manipulate the pressure upstream of said backpressure restrictor to restrict the flow of said carrier fluid through said carrier pre-heat device.

10. The gas chromatograph of claim 9, wherein said backpressure restrictor connects to said transport line downstream of said reference measurement location.

11. The gas chromatograph of claim 9, wherein said backpressure restrictor is additionally used to manipulate a flow profile downstream of said backpressure restrictor to result in the transport of a near-constant mass flow rate of fluid sample through said backpressure restrictor.

12. The gas chromatograph of claim 9, wherein said back pressure restrictor is tubing with the ratio of the pressure at a downstream end of said pressure restrictor to a pressure at an upstream end of said pressure restrictor being less than or slightly greater than 0.528.

13. The gas chromatograph of claim 9, wherein said back pressure restrictor is tubing having a pressure drop ratio of less than or equal to 0.528.

14. The gas chromatograph of claim 9, further comprising:
an insulated oven encapsulating said pre-heat coil; and
a heater within said insulated oven, and wherein said pre-heat device is a pre-heat coil.

15. The gas chromatograph of claim 9, wherein said backpressure restrictor is capillary tubing.

16. The gas chromatograph of claim 9, wherein said backpressure restrictor is capillary tubing having an inner diameter of less than 0.04".

17. The gas chromatograph of claim 9, wherein said component measurement element is a thermal conductivity detector.

18. A gas chromatograph, comprising:
a separation column with an upstream end and a downstream end, said separation column to elute a fluid sample into component parts;
a backpressure restrictor having an upstream end, said upstream end of said backpressure restrictor being connected to said downstream end of said separation column, said backpressure restrictor proximate enough to said separation column to reduce at least one of longitudinal diffusion and resistance to mass transfer in the mobile phase.

19. The gas chromatograph of claim 18, wherein said backpressure restrictor is capillary tubing.

20. The gas chromatograph of claim 18, wherein said backpressure restrictor is within about 10 inches downstream of said separation column.

21. The gas chromatograph of claim 18, wherein said backpressure restrictor is within about 8.3 inches downstream of said separation column.

22. The gas chromatograph of claim 18, wherein said backpressure restrictor is within about 5 inches downstream of said separation column.

23. A gas chromatograph, comprising:
a component measurement device including a reference measurement location and a fluid component measurement location;
a carrier pre-heat device connected to and upstream of said reference measurement location to carry and heat a flow of carrier gas; and
a backpressure restrictor downstream of said carrier pre-heat device and connected to said component measurement device, said backpressure restrictor being used to manipulate the flow profile downstream of said backpressure restrictor to result in the transport of a near-constant mass flow rate of fluid sample from said upstream end to said downstream end.

24. The gas chromatograph of claim 23, wherein said backpressure restrictor is downstream of both said carrier pre-heat device and said component measurement device.

25. The gas chromatograph of claim 23, wherein said component measurement device is a thermal conductivity detector.

26. The gas chromatograph of claim 23, wherein said backpressure restrictor is capillary tubing having an inner diameter of less than or equal to 0.04 inches.

27. A gas chromatograph, comprising:
a separation column to separate a fluid sample into component parts, said separation column having an upstream and a downstream end;
a measurement device connected to said downstream end of said separation column;
a backpressure restrictor connected between said separation column and said measurement device.

28. The gas chromatograph of claim 27, wherein said backpressure restrictor is more proximate said measurement device than said separation column.

29. The gas chromatograph of claim 27, further comprising:
a second separation column;
a second backpressure restrictor, said second back pressure restrictor connected between said second separation column and said measurement device.

30. The gas chromatograph of claim 1, wherein no fluid is introduced between said back pressure restrictor and said separation column.

31. The gas chromatograph of claim 1, wherein no fluid is bled away between said back pressure restrictor and said separation column.

32. A sample handling system for a gas chromatograph, comprising:
a back pressure restrictor with an upstream end and a downstream end, said back pressure restrictor carrying a fluid flow from said upstream end to said downstream end; and
separation column attached to said downstream end of said back pressure restrictor to elute said fluid into component parts,
wherein said fluid flow has a flow profile downstream of said backpressure restrictor and said backpressure restrictor controls said downstream flow profile at said separation column to result in the transport of a near-constant mass flow of said fluid through said separation column.

* * * * *